(12) United States Patent
Kim et al.

(10) Patent No.: US 9,243,237 B2
(45) Date of Patent: Jan. 26, 2016

(54) METHOD FOR MASS PRODUCTION OF FACTOR VII/VIIA

(75) Inventors: Chang Hwan Kim, Suwon-si (KR); Sung Kap Hong, Yongin-si (KR); Byung Sun Lee, Seoul (KR); Sung Hwan Hong, Seoul (KR); Se Chang Kwon, Seoul (KR)

(73) Assignee: HANMI SCIENCE CO., LTD, Hwaseong-si (KR)

( * ) Notice: Subject to any disclaimer, the term of this patent is extended or adjusted under 35 U.S.C. 154(b) by 114 days.

(21) Appl. No.: 13/881,974

(22) PCT Filed: Oct. 26, 2011

(86) PCT No.: PCT/KR2011/008040
§ 371 (c)(1),
(2), (4) Date: Jul. 3, 2013

(87) PCT Pub. No.: WO2012/057527
PCT Pub. Date: May 3, 2012

(65) Prior Publication Data
US 2013/0273634 A1    Oct. 17, 2013

(30) Foreign Application Priority Data
Oct. 26, 2010    (KR) .................. 10-2010-0104403

(51) Int. Cl.
*A61K 38/00*    (2006.01)
*C12N 9/64*    (2006.01)
*C07K 14/745*    (2006.01)

(52) U.S. Cl.
CPC ............ *C12N 9/6437* (2013.01); *C07K 14/745* (2013.01)

(58) Field of Classification Search
None
See application file for complete search history.

(56) References Cited

U.S. PATENT DOCUMENTS

2004/0185535 A1    9/2004   Wilson et al.
2009/0263866 A1    10/2009  Wilson et al.

FOREIGN PATENT DOCUMENTS

| CN | 101486761 A | 7/2009 |
|---|---|---|
| CN | 101605899 A | 12/2009 |
| EP | 0 200 421 A2 | 12/1986 |
| JP | 2010506586 A | 3/2010 |
| KR | 1997-0006499 B1 | 2/1997 |
| KR | 10-2002-0017501 A | 3/2002 |
| KR | 10-0880509 B1 | 1/2009 |
| WO | 2008/048037 A1 | 4/2008 |
| WO | 2010005227 A2 | 1/2010 |

OTHER PUBLICATIONS

Dorner et al. (JBC, 1989, vol. 264, No. 34, pp. 20602-20607).*
Korean Intellectual Property Office, Notice of Preliminary Rejection dated May 26, 2013, issued in counterpart Application No. 0-2011-0109882.
Taiwan Intellectual Property Office, Rejection Decision Letter dated Mar. 25, 2014, issued in the counterpart Application No. 100138824.
European Patent Office, Extended European Search Report dated Mar. 19, 2014, issued in counterpart Application No. 11836619.4.
Kruh, "Effects of sodium butyrate, a new pharmacological agent, on cells in culture", Molecular and Cellular Biochemistry vol. 42, No. 2, May 1982, p. 65-82.
Li, et al., "Butyrate induces profound changes in gene expression related to multiple signal pathways in bovine kidney epithelial cells", BMC Genomics, BioMed Central, vol. 7, No. 1, Sep. 14, 2006, p. 1-14.
R.D. Everett, et al., "The repeated GC-rich motifs upstream from the TATA box are important elements of the SV40 early promoter", Nucleic Acids Research, 1983, pp. 2447-2464, vol. 11, No. 8.
M. Fromm, et al., "Transcription in vivo from SV40 early promoter deletion mutants without repression by large T antigen", Journal of Molecular and Applied Genetics, 1983, pp. 127-135, vol. 2, No. 1.
William S. Dynan, et al., "The promoter-specific transcription factor Sp1 binds to upstream sequences in the SV40 early promoter", Cell, Nov. 1983, pp. 79-87, vol. 35, No. 1.
George J. Broze, Jr., et al., "Purification and Properties of Human Coagulation Factor VII,"The Journal of Biological Chemistry, Feb. 25, 1980, pp. 1242-1247, vol. 255, No. 4.
Japan Patent Office, Communication dated Sep. 15, 2015, issued in corresponding Japanese Application No. 2013-536513.

* cited by examiner

*Primary Examiner* — Hope Robinson
(74) *Attorney, Agent, or Firm* — Sughrue Mion, PLLC (57) ABSTRACT

A method for the mass production of human coagulation Factor VII. The method includes a) providing an expression vector carrying i) a dihydrofolate reductase promoter devoid of one or more CCGCC repeat sequences from the GC-rich region thereof and a dihydrofolate reductase (DHFR) gene operably linked thereto and ii) a cytomegalovirus (CMV) promoter and a human coagulation Factor VII gene operably linked thereto; b) obtaining a transformed host cell line containing the expression vector; and c) culturing the transfected host cell in the presence of a dihydrofolate reductase inhibitor to select cells which express human coagulation Factor VII with high efficiency; and d) adding sodium butyrate to the selected host cells.

8 Claims, 1 Drawing Sheet

SEQUENCE LISTING

```
<160> NUMBER OF SEQ ID NOS: 3

<210> SEQ ID NO 1
<211> LENGTH: 34
<212> TYPE: DNA
<213> ORGANISM: Artificial Sequence
<220> FEATURE:
<223> OTHER INFORMATION: Forward primer for VIIBHISS

<400> SEQUENCE: 1
cccggatcca tggtctccca ggccctcagg ctcc                         34

<210> SEQ ID NO 2
<211> LENGTH: 31
<212> TYPE: DNA
<213> ORGANISM: Artificial Sequence
<220> FEATURE:
<223> OTHER INFORMATION: Reverse primer for VIIXhoIAS

<400> SEQUENCE: 2
gggctcgagc tagggaaatg gggctcgcag g                            31

<210> SEQ ID NO 3
<211> LENGTH: 8299
<212> TYPE: DNA
<213> ORGANISM: Homo sapiens

<400> SEQUENCE: 3
gacggatcgg gagatccgac atgataagat acattgatga gtttggacaa accacaacta    60
gaatgcagtg aaaaaaatgc tttatttgtg aaatttgtga tgctattgct ttatttgtaa   120
ccattataag ctgcaataaa caagttaaca acaacaattg cattcatttt atgtttcagg   180 ttcagggggga ggtgtgggag gttttttaaa gcaagtaaaa cctctacaaa tgtggtatgg   240
ctgattatga tctctagtca aggcactata catcaaatat tccttattaa ccccttttaca   300 aattaaaaag ctaaaggtac acaattttttg agcatagtta ttaatagcag acactctatg   360
cctgtgtgga gtaagaaaaa acagtatgtt atgattataa ctgttatgcc tacttataaa   420
ggttacagaa tatttttcca taattttctt gtatagcagt gcagcttttt cctttgtggt   480
gtaaatagca aagcaagcaa gagttctatt actaaacaca gcatgactca aaaaacttag   540
caattctgaa ggaaagtcct tggggtcttc tacctttctc ttctttttttg gaggagtaga   600 atgttgagag tcagcagtag cctcatcatc actagatggc atttcttctg agcaaaacag   660
gttttcctca ttaaaggcat tccaccactg ctcccattca tcagttccat aggttggaat   720
ctaaaataca caaacaatta gaatcagtag tttaacacat tatacactta aaaattttat   780
atttacctta gagctttaaa tctctgtagg tagtttgtcc aattatgtca caccacagaa   840
```

```
gtaaggttcc ttcacaaaga tccaaagcca gcaaaagtcc catggtctta taaaaatgca     900
tagctttagg aggggagcag agaacttgaa agcatcttcc tgttagtctt tcttctcgta     960
gacttcaaac ttatacttga tgccttttc ctcctggacc tcagagagga cgcctgggta    1020
ttctgggaga agtttatatt tccccaaatc aatttctggg aaaaacgtgt cactttcaaa    1080
ttcctgcatg atccttgtca caagagtct gaggtggcct ggttgattca tggcttcctg    1140
gtaaacagaa ctgcctccga ctatccaaac catgtctact ttacttgcca attccggttg    1200
ttcaataagt cttaaggcat catccaaact tttggcaaga aaatgagctc ctcgtggtgg    1260
ttctttgagt tctctactga aactatatt aattctgtcc tttaaaggtc gattcttctc    1320
aggaatggag aaccaggttt tcctacccat aatcaccaga ttctgtttac cttccactga    1380
agaggttgtg gtcattcttt ggaagtactt gaactcgttc ctgagcggag ccagggtag    1440
gtctccgttc ttgccaatcc ccatattttg ggacacggcg acgatgcagt tcaatggtcg    1500
aaccatgatg gcagcgggga taaaatccta ccagccttca cgctaggatt gccgtcaagt    1560
ttggcgcgaa atcgcagccc tgagctgtgg atctcccgat cccctatggt gcactctcag    1620
tacaatctgc tctgatgccg catagttaag ccagtatctg ctccctgctt gtgtgttgga    1680
ggtcgctgag tagtgcgcga gcaaaattta agctacaaca aggcaaggct tgaccgacaa    1740
ttgcatgaag aatctgctta gggttaggcg ttttgcgctg cttcgcgatg tacgggccag    1800
atatacgcgt tgacattgat tattgactag ttattaatag taatcaatta cggggtcatt    1860
agttcatagc ccatatatgg agttccgcgt tacataactt acggtaaatg gcccgcctgg    1920
ctgaccgccc aacgaccccc gcccattgac gtcaataatg acgtatgttc ccatagtaac    1980
gccaataggg actttccatt gacgtcaatg ggtggagtat ttacggtaaa ctgcccactt    2040
ggcagtacat caagtgtatc atatgccaag tacgccccct attgacgtca atgacggtaa    2100
atggcccgcc tggcattatg cccagtacat gaccttatgg gactttccta cttggcagta    2160
catctacgta ttagtcatcg ctattaccat ggtgatgcgg ttttggcagt acatcaatgg    2220
gcgtggatag cggtttgact cacggggatt tccaagtctc cacccccattg acgtcaatgg    2280
gagtttgttt tggcaccaaa atcaacggga ctttccaaaa tgtcgtaaca actccgcccc    2340
attgacgcaa atgggcggta ggcgtgtacg gtgggaggtc tatataagca gagctctctg    2400
gctaactaga gaacccactg cttactggct tatcgaaatt aatacgactc actataggga    2460
gacccaagct tggtaccgag ctcggatcca tggtctccca ggcctcagg ctcctctgcc    2520
ttctgcttgg gcttcagggc tgcctggctg cagtcttcgt aacccaggag gaagccacg    2580
gcgtcctgca ccggcgccgg cgcgccaacg cgttcctgga ggagctgcgg ccgggctccc    2640
tggagaggga gtgcaaggag gagcagtgct ccttcgagga ggcccgggag atcttcaagg    2700
acgcggagag gacgaagctg ttctggattt cttacagtga tggggaccag tgtgcctcaa    2760
gtccatgcca gaatgggggc tcctgcaagg accagctcca gtcctatatc tgcttctgcc    2820
tccctgcctt cgagggccgg aactgtgaga cgcacaagga tgaccagctg atctgtgtga    2880
acgagaacgg cggctgtgag cagtactgca gtgaccacac gggcaccaag cgctcctgtc    2940
ggtgccacga ggggtactct ctgctggcag acggggtgtc ctgcacaccc acagttgaat    3000
atccatgtgg aaaaatacct attctagaaa aagaaatgc cagcaaaccc caaggccgaa    3060
ttgtgggggg caaggtgtgc cccaaagggg agtgtccatg gcaggtcctg ttgttggtga    3120
atggagctca gttgtgtggg gggaccctga tcaacaccat ctgggtggtc tccgcggccc    3180
```

```
actgtttcga caaaatcaag aactggagga acctgatcgc ggtgctgggc gagcacgacc    3240
tcagcgagca cgacggggat gagcagagcc ggcgggtggc gcaggtcatc atccccagca    3300
cgtacgtccc gggcaccacc aaccacgaca tcgcgctgct ccgcctgcac cagcccgtgg    3360
tcctcactga ccatgtggtg cccctctgcc tgcccgaacg gacgttctct gagaggacgc    3420
tggccttcgt gcgcttctca ttggtcagcg gctggggcca gctgctggac cgtggcgcca    3480
cggccctgga gctcatggtc tcaacgtgc cccggctgat gacccaggac tgcctgcagc    3540
agtcacggaa ggtgggagac tccccaaata tcacggagta catgttctgt gccggctact    3600
cggatgcag caaggactcc tgcaagggggg acagtggagg cccacatgcc acccactacc    3660
ggggcacgtg gtacctgacg ggcatcgtca gctggggcca gggctgcgca accgtgggcc    3720
actttgggt gtacaccagg gtctcccagt acatcgagtg gctgcaaaag ctcatgcgct    3780
cagagccacg cccaggagtc ctcctgcgag ccccatttcc ctagctcgag catgcatcta    3840
gagggccta ttctatagtg tcacctaaat gctagagctc gctgatcagc ctcgactgtg    3900
ccttctagtt gccagccatc tgttgtttgc cctcccccg tgccttcctt gaccctggaa    3960
ggtgccactc ccactgtcct ttcctaataa aatgaggaaa ttgcatcgca ttgtctgagt    4020
aggtgtcatt ctattctggg gggtggggtg ggcaggaca gcaaggggga ggattgggaa    4080
gacaatagca ggcatgctgg ggatgcggtg ggctctatgg cttctgaggc ggaaagaacc    4140
agctggggct ctaggggta tccccacgcg ccctgtagcg gcgcattaag cgcggcgggt    4200
gtggtggtta cgcgcagcgt gaccgctaca cttgccagcg ccctagcgcc cgctcctttc    4260
gctttcttcc cttcctttct cgccacgttc gccggctttc cccgtcaagc tctaaatcgg    4320
gggctccctt tagggttccg atttagtgct ttacggcacc tcgaccccaa aaaacttgat    4380
tagggtgatg gttcacgtag tgggccatcg ccctgataga cggtttttcg ccctttgacg    4440
ttggagtcca cgttctttaa tagtggactc ttgttccaaa ctggaacaac actcaaccct    4500
atctcggtct attcttttga tttataaggg attttgccga tttcggccta ttggttaaaa    4560
aatgagctga tttaacaaaa atttaacgcg aattaattct gtggaatgtg tgtcagttag    4620
ggtgtggaaa gtccccaggc tccccagcag gcagaagtat gcaaagcatg catctcaatt    4680
agtcagcaac caggtgtgga aagtccccag gctccccagc aggcagaagt atgcaaagca    4740
tgcatctcaa ttagtcagca accatagtcc cgcccctaac tccgcccatc ccgcccctaa    4800
ctccgcccag ttccgcccat tctccgcccc atggctgact aatttttttt atttatgcag    4860
aggccgaggc cgcctctgcc tctgagctat tccagaagta gtgaggaggc ttttttggag    4920
gcctaggctt ttgcaaaaag ctcccgggag cttgtatatc cattttcgga tctgatcaag    4980
agacaggatg aggatcgttt cgcatgattg aacaagatgg attgcacgca ggttctccgg    5040
ccgcttgggt ggagaggcta ttcggctatg actgggcaca acagacaatc ggctgctctg    5100
atgccgccgt gttccggctg tcagcgcagg ggcgcccggt tctttttgtc aagaccgacc    5160
tgtccggtgc cctgaatgaa ctgcaggacg aggcagcgcg gctatcgtgg ctggccacga    5220
cgggcgttcc ttgcgcagct gtgctcgacg ttgtcactga agcgggaagg gactggctgc    5280
tattgggcga agtgccgggg caggatctcc tgtcatctca ccttgctcct gccgagaaag    5340
tatccatcat ggctgatgca atgcggcggc tgcatacgct tgatccggct acctgcccat    5400
tcgaccacca agcgaaacat cgcatcgagc gagcacgtac tcggatggaa gccggtcttg    5460
tcgatcagga tgatctggac gaagagcatc agggctcgc gccagccgaa ctgttcgcca    5520
ggctcaaggc gcgcatgccc gacggcgagg atctcgtcgt gacccatggc gatgcctgct    5580
```

```
tgccgaatat catggtggaa aatggccgct tttctggatt catcgactgt ggccggctgg   5640
gtgtggcgga ccgctatcag gacatagcgt tggctacccg tgatattgct gaagagcttg   5700
gcggcgaatg ggctgaccgc ttcctcgtgc tttacggtat cgccgctccc gattcgcagc   5760
gcatcgcctt ctatcgcctt cttgacgagt tcttctgagc gggactctgg ggttcgaaat   5820
gaccgaccaa gcgacgccca acctgccatc acgagatttc gattccaccg ccgccttcta   5880
tgaaaggttg ggcttcggaa tcgttttccg ggacgccggc tggatgatcc tccagcgcgg   5940
ggatctcatg ctggagttct tcgcccaccc caacttgttt attgcagctt ataatggtta   6000
caaataaagc aatagcatca caaatttcac aaataaagca ttttttttcac tgcattctag   6060 ttgtggtttg tccaaactca tcaatgtatc ttatcatgtc tgtataccgt cgacctctag   6120
ctagagcttg gcgtaatcat ggtcatagct gtttcctgtg tgaaattgtt atccgctcac   6180
aattccacac aacatacgag ccggaagcat aaagtgtaaa gcctggggtg cctaatgagt   6240
gagctaactc acattaattg cgttgcgctc actgcccgct ttccagtcgg gaaacctgtc   6300
gtgccagctg cattaatgaa tcggccaacg cgcggggaga ggcggtttgc gtattgggcg   6360
ctcttccgct tcctcgctca ctgactcgct gcgctcggtc gttcggctgc ggcgagcggt   6420
atcagctcac tcaaaggcgg taatacggtt atccacagaa tcaggggata acgcaggaaa   6480
gaacatgtga gcaaaaggcc agcaaaaggc caggaaccgt aaaaaggccg cgttgctggc   6540 gttttccat aggctccgcc cccctgacga gcatcacaaa aatcgacgct caagtcagag    6600
gtggcgaaac ccgacaggac tataaagata ccaggcgttt ccccctggaa gctccctcgt   6660
gcgctctcct gttccgaccc tgccgcttac cggatacctg tccgcctttc tcccttcggg   6720
aagcgtggcg ctttctcata gctcacgctg taggtatctc agttcggtgt aggtcgttcg   6780
ctccaagctg ggctgtgtgc acgaaccccc cgttcagccc gaccgctgcg ccttatccgg   6840
taactatcgt cttgagtcca acccggtaag acacgactta tcgccactgg cagcagccac   6900
tggtaacagg attagcagag cgaggtatgt aggcggtgct acagagttct tgaagtggtg   6960
gcctaactac ggctacacta agaacagt atttggtatc tgcgctctgc tgaagccagt     7020
taccttcgga aaaagagttg gtagctcttg atccggcaaa caaaccaccg ctggtagcgg   7080
tggttttttt gtttgcaagc agcagattac gcgcagaaaa aaaggatctc aagaagatcc   7140
tttgatcttt tctacggggt ctgacgctca gtggaacgaa aactcacgtt aagggatttt   7200
ggtcatgaga ttatcaaaaa ggatcttcac ctagatcctt ttaaattaaa aatgaagttt   7260
taaatcaatc taaagtatat atgagtaaac ttggtctgac agttaccaat gcttaatcag   7320
tgaggcacct atctcagcga tctgtctatt tcgttcatcc atagttgcct gactccccgt   7380
cgtgtagata actacgatac gggagggctt accatctggc cccagtgctg caatgatacc   7440
gcgagaccca cgctcaccgg ctccagattt atcagcaata aaccagccag ccggaagggc   7500
cgagcgcaga agtggtcctg caactttatc cgcctccatc cagtctatta attgttgccg   7560
ggaagctaga gtaagtagtt cgccagttaa tagtttgcgc aacgttgttg ccattgctac   7620
aggcatcgtg gtgtcacgct cgtcgtttgg tatggcttca ttcagctccg gttcccaacg   7680
atcaaggcga gttacatgat cccccatgtt gtgcaaaaaa gcggttagct ccttcggtcc   7740
tccgatcgtt gtcagaagta agttggccgc agtgttatca ctcatggtta tggcagcact   7800
gcataattct cttactgtca tgccatccgt aagatgcttt tctgtgactg gtgagtactc   7860
aaccaagtca ttctgagaat agtgtatgcg gcgaccgagt tgctcttgcc cggcgtcaat   7920
```

-continued

```
acgggataat accgcgccac atagcagaac tttaaaagtg ctcatcattg gaaaacgttc    7980
ttcggggcga aaactctcaa ggatcttacc gctgttgaga tccagttcga tgtaacccac    8040
tcgtgcaccc aactgatctt cagcatcttt tactttcacc agcgtttctg ggtgagcaaa    8100
aacaggaagg caaaatgccg caaaaaaggg aataagggcg acacggaaat gttgaatact    8160
catactcttc cttttcaat attattgaag catttatcag ggttattgtc tcatgagcgg     8220
atacatattt gaatgtattt agaaaaataa acaaataggg gttccgcgca catttccccg    8280
aaaagtgcca cctgacgtc                                                 8299
```

METHOD FOR MASS PRODUCTION OF FACTOR VII/VIIA

CROSS REFERENCE TO RELATED APPLICATIONS

This application is a National Stage of International Application No. PCT/KR2011/008040, filed on Oct. 26, 2011, which claims priority from Korean Patent Application No. 10-22010-0104403, filed on Oct. 26, 2010, the contents of all of which are incorporated herein by reference in their entirety.

TECHNICAL FIELD

The present invention relates to a method for the mass production of human coagulation factor VII, comprising: a) constructing an expression vector carrying i) a dihydrofolate reductase promoter devoid of one or more CCGCC repeat sequences from the GC-rich region thereof and a dihydrofolate reductase (DHFR) gene operably linked thereto and ii) a cytomegalovirus (CMV) promoter and a human coagulation factor VII gene operably linked thereto; b) transfecting the expression vector of step a) into an animal cell line; c) culturing the transfected animal cell line of step b) in the presence of a dihydrofolate reductase inhibitor to select cells which express human coagulation factor VII with high efficiency; and d) adding sodium butyrate to the selected animal cells of step c), and a cell line for mass production of human coagulation factor VII.

BACKGROUND ART

Coagulation factor VII (FVII) is a precursor of serine protease that causes blood to clot in the coagulation cascade where it activates coagulation factor X or factor IX. FVII, produced in the liver, is a glycoprotein which consists of a single chain with a molecular weight of 50,000 Da. When decomposed into two chains by different proteases, among which are factor Xa, factor XIIa, factor IXa and thrombin, FVII is itself activated into an active form, FVIIa. FVII is also activated to FVIIa by binding to tissue factors and negatively charged phospholipid A (Nemerson et al, Thromb. Res, 1985, 40:351~358). In the presence of tissue factor and calcium ions, FVIIa activates factor X into factor Xa which, in turn, convert prothrombin into thrombin with the aid of factor Va in the presence of calcium ion and phospholipid, performing coagulation.

Factor VII, consisting of 406 amino acids, is cleaved at the peptide bond between arginine 152 and isoleucine 153 to form factor VIIa in which the light chain (152 amino acids) and the heavy chain (254 amino acids) are held together by a disulfide bond. The light chain comprises one gamma carboxyl glutamic acid domain (Gla) and two EGF (epidermal growth factor) domains while the heavy chain is responsible for serine protease activity.

In order for Factor VII to be fully functional, it must be subjected to gamma-carboxylation of 10 n-terminal glutamic acid residues, which is a vitamin-K dependent process (Hagen et al, Natl. Acad. SC. U.S.A, 1986, 83:2412~2416). This Gla-domain is known to be involved in binding factor VII to the cell surface containing the tissue factor (Sakai et al, J. Biol Chem, 1990, 265:1890~1894).

To date, there are two approaches to the production of factor VIIa. In one approach, factor VII is isolated and purified from plasma and activated to VIIa (Broze et al, J. Biol. Chem, 1980, 225:1242~1247). The other is a genetic engineering technique in which animal cells transformed with a DNA sequence of factor VII are cultured to produce factor VII (European Patent Application No: 86302855.1).

The plasma-derived factor VIIa suffers from the disadvantage of having a low production yield and lacking consistency in supply. A particular problem with this factor lies in the risk it poses to the safety of the body. In contrast, the genetic recombinant product is considered to overcome the demerits of the plasma-derived product.

However, animal cells from which factor VII is produced by genetic recombination generally have a low expression level, so that only low productivity can be guaranteed. Hence, in order for factor VII to be used as a therapeutic agent, it is necessary to secure a cell line in which the factor can be stably produced on mass scale. In this context, an expression vector that has high expression efficiency is indispensable.

DISCLOSURE

Technical Problem

Leading up to the present invention, intensive and thorough research into the mass production of factor VII, conducted by the present inventors, resulted in the finding that an expression vector with a dihydrofolate reductase (DHFR) promoter devoid of the GC-rich repeating sequence allows animal cells to be transformed into those capable of stably expressing factor VII with high efficiency, as measured by a series of experiments in which the expression vector was transfected into an animal cell line to give a single-cell transformant and when the single-cell transformant was cultured in the presence of a broad concentration spectrum of sodium butyrate, wherein the expression of factor VII was significantly increased at a relatively high concentration of sodium butyrate.

Technical Solution

It is an object of the present invention to provide a method for producing factor VII, comprising: a) constructing an expression vector carrying i) a dihydrofolate reductase promoter devoid of one or more CCGCC repeat sequences from the GC-rich region thereof and a dihydrofolate reductase (DHFR) gene operably linked thereto and ii) a cytomegalovirus (CMV) promoter and a human coagulation factor VII gene operably linked thereto; b) transfecting the expression vector of step a) into an animal cell line; c) culturing the transfected animal cell line of step b) in the presence of a dihydrofolate reductase inhibitor to select cells which express human coagulation factor VII with high efficiency; and d) adding sodium butyrate to the selected animal cells of step c).

It is another object of the present invention to provide a cell line for producing factor VII.

Advantageous Effects

Employing a vector carrying a DHFR promoter devoid of GC-rich repeating sequences, the present invention can produce human coagulation factor VII at high efficiency on a large scale, which contributes to the treatment of hemophilia.

BEST MODE

In accordance with an aspect thereof, the present invention provides a method for the mass production of human coagulation factor VII, comprising: a) constructing an expression vector carrying i) a dihydrofolate reductase promoter devoid of one or more CCGCC repeat sequences from the GC-rich region thereof and a dihydrofolate reductase (DHFR) gene operably linked thereto and ii) a cytomegalovirus (CMV) promoter and a human coagulation factor VII gene operably linked thereto; b) transfecting the expression vector of step a) into an animal cell line; c) culturing the transfected animal cell line of step b) in the presence of a dihydrofolate reductase inhibitor to select cells which express human coagulation factor VII with high efficiency; and d) adding sodium butyrate to the selected animal cells of step c).

Preferably, step a) addresses constructing an expression vector carrying i) a dihydrofolate reductase promoter devoid of one or more CCGCC repeat sequences from the GC-rich region thereof and a dihydrofolate reductase (DHFR) gene operably linked thereto and ii) a cytomegalovirus (CMV) promoter and a human coagulation factor VII gene operably linked thereto.

The term "GC-rich region," as used herein, refers to the CCGCC sequence repeated in the dihydrofolate reductase promoter. When all or a part of this repeating sequence is artificially defected by deletion or mutation, the level of dihydrofolate reductase expression is at a minimum. Under this condition, the presence of a dihydrofolate inhibitor causes the cells to amplify the dihydrofolate reductase gene at a greater frequency for survival, thus resulting in the simultaneous high expression of a gene of interest carried by an expression vector containing the dihydrofolate reductase gene.

According to an embodiment thereof, therefore, the present invention provides a high expression-inducing cassette comprising a dihydrofolate reductase promoter devoid of one or more CCGCCC repeating sequences and a dihydrofolate reductase gene. Preferably, the high expression-inducing cassette comprises a dihydrofolate reductase promoter in which the CCGCCC repeating sequence is repeated six times or less, more preferably three times or less, more particularly preferable once or less, and even more particularly preferable is when it is absent.

The removal of these CCGCCC repeating sequences can be achieved by genetically recombinant substitution or deletion techniques widely known in the art. In one embodiment of the present invention, a part of a base sequence containing the CCGCCC repeating sequences is deleted to remove a part or all of the GC-rich region from the promoter.

As used herein, the term "dihydrofolate reductase" refers to an enzyme that reduces dihydroloic acid to tetrahydrofolic acid with NADPH serving as an electron donor. In humans, the DHFR gene encodes the enzyme.

The term "human coagulation factor" or just "factor," as used herein, refers to a protein which is involved in blood coagulation upon hemorrhage, thereby offering protection. The term "coagulation" refers to a complex process in which blood forms clots and in which 12 factors participate. The present invention is directed to the mass production of factor VII.

The term "factor VII," as used herein, refers to a heat-unstable protein with a molecular weight of 50,000 Da, also known as proconvertin, which is produced in the liver and ranges in serum level from 20 to 40 mg/mL. For use in coagulation, factor VII should be activated to an active form, that is, factor VIIa. The factor VII encoded by a gene that shares a sequence homology of 70% or greater, preferably 80% or greater, more preferably 90% or greater, much more preferably 95% or greater, and most preferably 97% or greater with the wild-type factor VII gene is within the scope of the present invention. Preferable is factor VII encoded by the gene of SEQ ID NO: 3.

Figure 1:
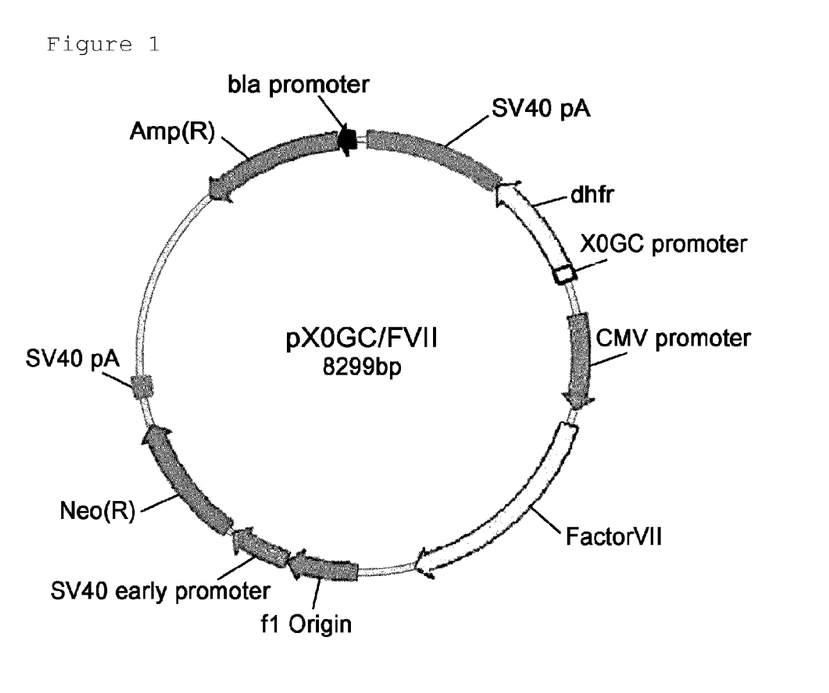
FIG. 1 shows a construction process and map of an hFVII expression vector.

The term "vector," as used herein, refers to any vehicle for the cloning of and/or transfer of a nucleic acid into a host cell. A vector may be a replicon to which another DNA segment may be attached so as to bring about the replication of the attached segment. A "replicon" refers to any genetic element (e.g., plasmid, phage, cosmid, chromosome, virus) that functions as an autonomous unit of DNA replication in vivo, i.e., that is capable of replication under its own control. The term "vector" includes both viral and non-viral vehicles for introducing the nucleic acid into a host cell in vitro, ex vivo, or in vivo. The term "vector" may also include minicircle DNAs. For example, the vector may be a plasmid without bacterial DNA sequences. The removal of bacterial DNA sequences that are rich in CpG regions has been shown to decrease transgene expression silencing and result in more persistent expression from plasmid DNA vectors (see e.g., Ehrhardt, A. et al. (2003) Hum Gene Ther 10: 215-25; Yet, N. S. (2002) Mol Ther 5: 731-38; Chen, Z. Y. et al. (2004) Gene Ther 11: 856-64). The term "vector" may also include transposons such as Sleeping Beauty (Izsvak et al. J. Mol. Biol. 302:93-102 (2000)), or artificial chromosomes. As used herein, the term "expression vector" means a vector that can express a protein of interest, e.g., the factor, at high efficiency. In the present invention, the expression vector contains i) a dihydrofolate reductase (DHFR) promoter devoid of one or more CCGCCC repeating sequences from the GC-rich region thereof, and a dihydrofolate reductase (DHFR) gene operably linked thereto. Preferably, the expression vector may be the pXOGC-FVII illustrated in FIG. 1. Examples of the expression vector useful in the present invention include plasmids, cosmids, bacteriophages, adenovirus vector, retrovirus vectors, and adeno-associated virus vectors, with a preference for plasmids.

Preferably, the expression vector may further include a gene encoding a human coagulation factor VII. The human coagulation factor VII may be expressed at high levels by expressing the expression vector.

The human coagulation factor VII may be expressed under the control of the DHFR gene promoter or under the control of an independent promoter. Preferably, the human coagulation factor VII may be placed under the control of an independent promoter. Such promoters include those widely known in the art, and non-limiting examples of such promoters include cytomegalovirus (CMV) promoter, LTR promoter, EFa promoter, SV40 promoter and TK promoter. Those skilled in the art will readily select any one from the group consisting of the aforementioned promoters.

The expression vector of the present invention, which is provided for inducing high expression of a gene of human coagulation factor VII in animal cells, may preferably further include a resistance gene for animal cells, which is used as a selectable marker for permanent expression of the gene in animal cells. Non-limiting examples of such resistance genes for animal cells include those commonly used in the art, such as the neomycin resistance gene, the zeomycin resistance gene, the hygromycin resistance gene, and the blastomycin resistance gene.

As well, the expression vector of the present invention may further include, but is not limited to, general constituent elements of a vector, such as a replication origin and a polyadenylation signal, and other transcriptional control elements.

Preferably, step (b) addresses the transformation of an animal cell line with the expression vector of step a).

As used herein, the term "transformation" or "transfection" in all its grammatical forms and spelling variations refers to the artificial genetic alteration of a cell resulting from the introduction of a foreign gene to the host cell so that the introduced gene can replicate by itself or as a factor incorporated into the chromosome.

The vector of the present invention can be introduced into host cells using suitable standard techniques known in the art, examples of which include electroporation, calcium phosphate co-precipitation, retroviral infection, microinjection, DEAE-dextran, and cationic liposome calcium, but are not limited thereto.

In the present invention, for example, an expression vector carrying a recombinant gene is transformed into CHO cells with the aid of Lipofectamine.

A procedure for culturing animal cell lines may be conducted using any medium and culture conditions well known in the art that are suitable. Those skilled in the art can readily control the culturing procedure to correspond to the strains employed. For example, the procedure may involve suspension culturing or an attachment culturing method according to the growth type of cells, which may be performed in a batch type, in a continuous type, or in a fed-batch type. The culture medium must adequately meet the specific requirements of the cell lines to be grown.

A culture medium for animal cells may contain a carbon source, a nitrogen source and trace elements. Examples of the carbon source include carbohydrates such as glucose, sucrose, lactose, fructose, maltose, starch and cellulose, oils and fats such as soybean oil, sunflower oil, castor oil and coconut oil, fatty acids such as palmitic acid, stearic acid and linoleic acid, alcohols such as glycerol and ethanol, and organic acids such as acetic acid. These carbon sources may be present solely or in combination in the culture medium. As a nitrogen source, an organic material such as peptone, yeast extract, broth, malt extract, corn steep liquor (CSL) and soybean, or an inorganic nitrogen compound such as urea, ammonium sulfate, ammonium chloride, ammonium phosphate, ammonium carbonate and ammonium nitrate may be contained in the culture medium. These nitrogen sources may be used solely or in combination. Besides, the culture medium may contain amino acids, vitamins and suitable precursors.

In addition, the medium may be supplemented with a DHFR inhibitor, such as methotrexate. This is, as described above, because the present invention aims to effectively establish in a short time a system by which a DHFR gene carried in a vector is amplified and selected by transforming DHFR-deficient animal cells with an expression vector according to the present invention and dosing the cells with a DHFR inhibitor so as to amplify a recombinant gene.

In a preferred embodiment, the concentration of the DHFR inhibitor that is used is preferably as low as possible for a short period of time for the sake of the production cost and the stability of cell lines. That is, the use of a low concentration of the DHFR inhibitor ensures the stable mass production of the protein of interest and reduces the time it takes to develop an expression cell line. In detail, the present invention provides a method of producing a human coagulation factor VII by transforming DHFR-deficient CHO cells with the recombinant protein expression vector and dosing the cells with less than 100 nM methotrexate, and preferably less than 50 nM methotrexate.

The recombinant protein of interest requires animal cells for its expression. In light of the purpose of the present invention, examples of suitable animal cells include Chinese hamster ovarian carcinoma (CHO) cells, monkey kidney cells (COST), NSO cells, SP2/0 cells, W138 cells, baby hamster kidney (BHK) cells, MDCK cells, myeloma cells, HuT 78 cells, and 293 cells, but are not limited thereto. Those skilled in the art can readily select an animal cell line suitable for use in the DHFR-based amplification system according to the present invention. Preferable in the present invention may be a cell deficient in dihydrofolate reductase.

The term "host cell transformed with a recombinant vector," as used herein, refers to a host cell that anchors therein a recombinant vector carrying a gene of interest. The host cell suitable for use in the present invention may originate from rodent cells or mammal cells, preferably animal cells or animal-derived cells, and most preferably CHO cells. When the purpose is to stably express the gene of interest and to amplify the copy number of the gene in a cell, a vector (e.g., pCHOI) having a DHFR gene that compensates for the deficiency may be introduced into a CHO cell deficient in nucleic acid synthetic pathways, and amplified with methotrexate (MTX).

The term "host" in the present invention encompasses an animal. For animals, various production systems utilizing a mammal or an insect are available. The mammals include goats, pigs, sheep, mice and cattle (Vicki Glaser, SPECTRUM Biotechnology Applications, 1993). In addition, the mammal may also include a transgenic animal. Further, a silkworm may be used as a host insect. The silkworm is infected with a baculovirus into which DNA encoding a desired protein has been inserted. The desired protein can be obtained from the body fluid of the silkworm (Nature, Vol. 315, p. 592-594, 1985). Preferably, CHO cells are used as host cells in the present invention.

In detail, a dihydrofolate reductase (DHFR)-deficient Chinese hamster ovarian carcinoma cell line (CHO/dhfr−) was used. That is, DHFR-deficient CHO cells were transformed with an expression vector carrying a gene encoding human coagulation factor VII according to the present invention. In the transformed CHO cells, the gene was found to be amplified to a sufficient number of copies even at a methotrexate concentration of less than 100 nM, and even less than 50 nM, which was preferable. Thus, the present invention provides such an animal cell line.

In accordance with the present invention, step c) addresses culturing the transformed animal cell line of step b) in the presence of a dihydrofolate reductase inhibitor to select a cell line expressing factor VII at high efficiency.

More preferable may be HMF708 (KCTC 11779BP). The HMF708 cell line was deposited with the KCTC (Genetic Resources Center, KRIBB, 111 Gwahak-ro, Yuseong-gu, Daejeon, Korea) on Oct. 25, 2010, under accession No. KCTC 11779BP. The selected cell line was assimilated to suspension culture using a serum-free medium (EX-CELL CHO medium, Sigma, U.S.A., Cat. No. 14360C).

In accordance with the present invention step (d) addresses the addition of sodium butyrate to the selected animal cell line of step c) to induce the mass production of factor VII.

Sodium butyrate inhibits histone diacetylase, resulting in histone hyperacetylation. It has various effects on cultured mammalian cells including inducing differentiation and gene expression. In the present invention, the compound is used as an additive to induce the mass production of factor VII. In this context, the amount thereof can be readily determined by those skilled in the art and is preferably on the order of 0.1 to 3.0 mM and more preferably on the order of 0.1 to 1.5 mM.

According to an embodiment thereof, the present invention provides for the construction of two inducible high-expression cassettes, one of which contains only one of the CCGCCC repeat sequences of the DHFR promoter and the other of which contains none thereof, and *E. coli* cell lines transformed with these cassettes. The *E. coli* transformants were deposited with the KCTC (Korean Collection for Type Cultures; Genetic Resources Center, Korean Research Institute of Bioscience and Biotechnology (KRIBB), Yuseong-gu, Daejeon, Korea) on Oct. 2, 2006 under accession numbers KCTC 10991 BP and KCTC 10992 BP, respectively. In order to induce the high expression of a recombinant protein of interest, the inducible high-expression cassettes were isolated from the *E. coli* cell lines and genetically manipulated to carry a gene encoding a human coagulation factor VII protein to construct a recombinant expression vector. The vector pXOGC-FVII, shown in FIG. 1, may be preferably used as an expression vector which can allow a human coagulation factor VII protein to be produced in CHO cells in a culture medium supplemented with sodium butyrate.

A base sequence encoding the factor VII produced according to the present invention may preferably be the sequence of SEQ ID NO: 3.

The human coagulation factor VII protein may be expressed under the control of the DHFR gene promoter or under the control of a separate promoter. Preferably, the human coagulation factor VII protein may be placed under the control of an independent promoter. This may be one well known in the art, and may be readily selected from among, for example, cytomegalovirus (CMV) promoter, LTR promoter, EFα promoter, SV40 promoter and TK promoter by those skilled in the art.

When factor VII is produced in the aforementioned cell line, the method may further comprise purifying factor VII on a large scale.

Also, the method may further comprise activating produced factor VII to factor VIIa.

In an embodiment of the present invention, the GC-rich sequences of the DHFR promoter were rendered inactive so as to minimize DHFR expression, followed by adding a DHFR inhibitor to induce the DHFR gene to be amplified. Transformed cells in which gene amplification occurred were subjected to limiting dilution in order to obtain clonal populations derived from single cells. The single-cell clones thus obtained were cultured in a serum-free medium containing sodium butyrate on a large scale to produce factor VII. In addition, purifying factor VII and activating factor VII were carried out.

In accordance with another aspect, the present invention provides a cell line for producing human coagulation factor VII. More preferable may be HMF708 (KCTC 11779BP).

MODE FOR INVENTION

A better understanding of the present invention may be obtained through the following examples which are set forth to illustrate, but are not to be construed as limiting the present invention.

Example 1

Construction of Expression Vector (pX0GC-FVII) for Recombinant Factor VII

<1-1> Amplification of Factor VII

For use in inducing the overexpression of recombinant factor VII in animal cells, an expression vector was constructed. A human factor VII gene containing a signal sequence was obtained using PCR (polymerase chain reaction). The amplification of a factor VII gene was performed using forward and reverse primers of SEQ ID NOS: 1 and 2, with the human fetal liver cDNA library (purchased from Clontech USA, now incorporated into TAKARA BIO USA) serving as a template. For the convenience of cloning, the forward and the reverse primer were designed to have BamHI and XhoI restriction enzyme sites, respectively. These primers are given in Table 1, below.

TABLE 1

Primers for Amplifying Human Factor VII Gene

| Factor VII Primer | Base Sequence | SEQ ID NO |
|---|---|---|
| Forward (VIIBHISS) | Cccggatccatggtctcccaggccctcaggctcc | 1 |
| Reverse (VIIXhoIAS) | gggctcgagctagggaaatggggctcgcagg | 2 |

A mixture comprising the cDNA library (100 ng), the primers, dNTP, and pFX polymerase (Invitrogen) was placed in a PCR tube and was then subjected to PCR which started with denaturation at 95° C. for 1 min and then was performed with 30 cycles of denaturation at 95° C. for 30 sec, annealing at 60° C. for 30 sec and extension at 68° C. for 90 sec, followed by extension at 68° C. for 5 min. The 1.3 kb-long PCR product thus obtained was identified to have the base sequence of SEQ ID NO: 3 by DNA sequencing.

<1-2> Construction of Recombinant Factor VII Expression Vector (pX0GC-FVII)

In order to be placed under the control of a CMV promoter, the PCR product of factor VII, prepared in Example <1-1>, was ligated to the animal expression vector pX0GC. The pX0GC vector is an expression vector in which a DHFR promoter devoid of one or more CCGCCC repeating sequences is operably linked to a DHFR gene so as to induce the high expression of a recombinant protein of interest (refer to Korean Patent No. 880509).

The 1.3 kb-long factor VII gene obtained by PCR was digested at 37° C. for 2 hours with BamHI and XhoI and purified using a PCR purification kit (Qiagen USA). Separately, the animal expression vector pX0GC was also digested with the same restriction enzymes, that is, BamHI and XhoI under the same conditions as mentioned above, and purified by electrophoresis. These DNA segments were ligated to each other in the presence of T4 DNA ligase to form a recombinant vector, named pX0GC-FVII.

Example 2

Establishment of Human Factor VII Expressing Cell Line

<2-1> Transformation of Cell Line

To prepare a new cell line which can produce human factor VII on a mass scale, the recombinant human factor VII expression vector (pX0GC-FVII), constructed in Example 1 was introduced into the CHO cell line which showed unstable DNA synthesis due to the deficiency of DHFR (CHO/dhfr−) (Urlaub et al., Somat. Cell. Mol. Genet., 12, 555-566, 1986). In this regard, DG44-CHO (dhfr deficient) cells (obtained from Dr. Chasin, Columbia University) were cultured in T75 flasks and when grown to 80-90 confluence, the cells were transfected using Lipofectamine (Gibco, Cat. No. 18324-012). In each of two tubes was placed 3 mL of Opti-MEM (Gibco, Cat. No. 51985034). Then, the two tubes received 5

µg of DNA and 20 µl of Lipofectamine, respectively and were left to stand for 30 min. These two solutions were mixed together, and the DNA-Lipofectamine complex thus formed was dropped onto the cells which were previously washed three times with Opti-MEM medium. The cells were incubated at 37° C. for 18 hours in a 5% $CO_2$ incubator, washed three times with DMEM-F12 (Gibco, Cat. No. 11330) supplemented with 10% fetal bovine serum (BSA), and again cultured for 48 hours in a culture medium. When grown to almost full confluence, the cells were harvested by trypsinization. In order to select transformants, the cells were seeded onto new culture flasks containing an MEM-α selection medium (WELGENE, Cat. no. LM008-02) supplemented with 10% dialyzed FBS and 1 mg/mL G418 (Cellgro Cat No. 61-234-RG) and free of HT (Hypoxanthine-Thymidine) supplement. The cells were cultured with a fresh medium exchanged every 2 or 3 days until transformed cells survived to form colonies.

<2-2> Identification of human factor VII Expression Using Enzyme Immunoassay

The transformed cells of Example <2-1> were seeded at a density of $2\times10^4$ cells/well to 24-well plates. When the cells were grown to almost full confluence, serum-free CHO-A-SFM (Gibco, Cat. No. 05-5072EF) supplemented with 0.3 mM sodium butyrate (Sigma, Cat. No. B5887) was aliquoted in an amount of 200 µL/well, followed by incubation at 33° C. for 48 hours in a 5% $CO_2$ incubator. The cell culture was transferred to 1.5 mL tubes and centrifuged. Expression levels of human factor VII in the supernatants were measured by taking measurements using an enzyme immunoassay kit (American Diagnostica, Cat. no. 877) according to the manufacturer's instruction. In detail, the cell culture and the standard substance enclosed in the kit were diluted to certain concentrations in physiological saline containing 0.05% Tween-20, and the dilutions were added in an amount of 100 µL to each well of the kit and allowed to react at room temperature for one hour on a plate shaker. After being washed four times with the washing solution enclosed in the kit, each of the wells was incubated at room temperature for one hour with 100 µL of an anti-human factor VII antibody on a plate shake. Each well was again washed four times with the washing solution and then incubated at room temperature for 30 min with 100 µL of an HRP (horseradish peroxidase)-conjugated antibody to the anti-human factor VII antibody. Subsequently, the wells were washed four times, and incubated with 100 µL of a substrate per well at room temperature. Five minutes later, 50 µL of a stopping solution was added to each well, followed by measuring absorbance at 450 nm. A standard curve and a function were obtained from the concentrations of the standard solution and the absorbance values obtained. The curve was used to quantify the human factor VII, indicating that the selected cells expressed a certain level of human factor VII.

<2-3> Selection of Human Factor VII-Expressing Cell Line

Figure 2:
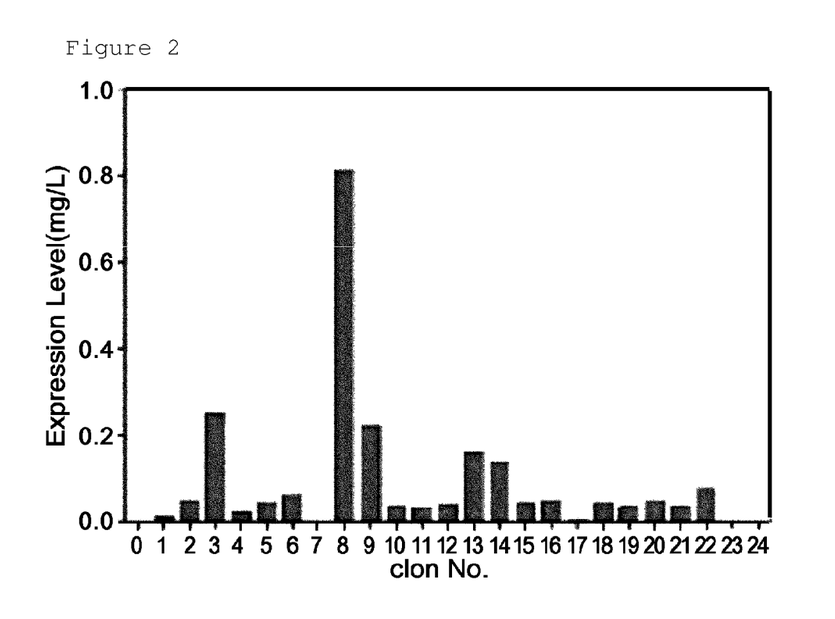
FIG. 2 is a graph showing hFVII expression levels in colonies formed from a cell line transformed with an hFVII expression vector, as measured by ELISA.

To increase the expression level of human factor VII in the cells which were identified to express human factor VII in Example <2-2>, the cells selected by a selection medium containing 10 nM MTX (Methotrexate, Sigma, Cat. No. M8407) were cultured for two weeks in T75 culture flasks with a passage every three days. A part of the cells in each well were transferred to 24-well plates and incubated in the same manner as in Example <2-2> before the determination of expression levels of human factor VII. Because the expression level of human factor VII was not increased at a concentration of 10 nM or higher, single-cell clones were isolated by limiting the dilution method in order to reduce heterogeneity at this point. That is, clones with heterogeneous expression levels of human factor VII were separated into single-cell clones whose human factor VII had a homogeneous expression level and which showed high productivity. In this regard, the cells in the well that had been identified as showing the highest expression level among the cells of the 6-well plates were diluted to a density of not more than one cell per well of 96-well plates, and only one cell seeded per well was cultured for 2-3 weeks. Afterwards, the cells were isolated from the well plates where colonies were formed, and sub-cultured before determining the expression level of human factor VII by an enzyme immunoassay method (FIG. 2). Among the cell lines separated by the limiting dilution method, a recombinant CHO which exhibited a stable proliferation trait and high productivity of human factor VII in the presence of 10 nM MTX was finally selected and named HMF708. The HMF708 strain was deposited with the KCTC (Genetic Resources Center, KRIBB, 111 Gwahak-ro, Yuseong-gu, Daejeon, Korea) on Oct. 25, 2010, under accession No. KCTC11779BP. The selected cell line was assimilated to a suspension culture using a serum-free medium (EX-CELL CHO medium, Sigma, U.S.A., Cat. No. 14360C).

Example 3

Growth of the Cell Line in the Presence of Sodium Butyrate and Measurement of hVII Level (1)

<3-1> Seed and Main Culture

One vial ($1\times10^7$ cells/mL) of the hFVII-expressing cell line which had been selected and assimilated to a suspension culture in Example <2-3> was taken from a liquid nitrogen tank and thawed as soon as possible in a 37° C. bath. After being washed once with a seed culturing medium (EX-CELL CHO medium (Sigma, Cat. No. 63225C) supplemented with 0.3 g/L glutamine), the cell culture was centrifuged at 90×g for 5 min and then inoculated into 50 mL of a seed culture medium in an Erlenmeyer flask (Corning, USA cat#431144). When grown for 1-2 days to a density of $10\times10^5$ cells/mL in a $CO_2$ incubator (37° C., 5% $CO_2$), the cells were centrifuged again in the same manner and then sub-cultured in 100 mL of a fresh seed culture medium in a new Erlenmeyer flask. The double-volume passage was continued until there was a sufficient number of cells.

<3-2> Growth of the Cell Line in Production Medium Containing Sodium Butyrate and Measurement of hFVII Level The effect of sodium butyrate on the production of hFVII was examined. For this, first, the recombinant CHO cell line which was being cultured was inoculated at a density of $5.0\times10^6$ cells/mL into 50 mL of a production medium in each of three Erlenmeyer flasks which contained sodium butyrate (Cat. no. B5887, SIGMA, USA) at concentrations of 0.3, 1.0 and 1.5 mM, respectively. The cells grown in the presence of 0.3 mM sodium butyrate were used as a control for comparison. The cells were cultured at 30.0° C. for four days to produce hFVII. On day 4, the cell concentration and cellular activity of the cell cultures were examined. There were no changes in cell density and cellular activity among the cell cultures of different butyrate concentrations.

In addition, after centrifugation of the cell cultures on Day 4, the levels of hFVII in the supernatants were measured using an enzyme immunoassay method as in Example <2-2>. Measurements are expressed as % of production compared to the control and summarized in Table 2, below.

TABLE 2

Production Level of hFVII according to
Concentration of Sodium Butyrate (%)

| Conc. of Na Butyrate (mM) | FVII Level (% compared to control %) | Final Cell Density (% compared to control) | Cellular Activity (% compared to control) |
|---|---|---|---|
| 0.3 | 100.0 | 100.0 | 100.0 |
| 1.0 | 164.9 | 106.8 | 100.2 |
| 1.5 | 190.1 | 108.5 | 99.9 |

As can be seen, the production of hFVII increased in a sodium butyrate dose-dependent manner.

Example 4

Growth of the Cell Line in Presence of Sodium Butyrate and Measurement of hFVII Level (2)

<4-1> Seed and Main Culture

One vial (1×10⁷ cells/mL) of the hFVII-expressing cell line which had been selected and assimilated to suspension culture in Example <2-3> was taken from a liquid nitrogen tank and thawed as soon as possible in a 37° C. bath. After being washed once with a seed culturing medium (EX-CELL CHO medium (Sigma, Cat. No. 63225C) supplemented with 0.3 g/L glutamine), the cell culture was centrifuged at 90×g for min and then inoculated into 50 mL of a seed culture medium in an Erlenmeyer flask (Corning, USA cat#431144). When grown for 1-2 days to a density of 10×10⁵ cell/mL in a $CO_2$ incubator (37° C., 5% $CO_2$), the cells were centrifuged again in the same manner and then sub-cultured in 100 mL of a fresh seed culture medium in a new Erlenmeyer flask. The double-volume passage was continued until a sufficient number of cells were achieved.

<4-2> Growth of the Cell Line in Mass-Scale Production Medium Containing Sodium Butyrate and Measurement of hFVII Level The effect of sodium butyrate on the production of hFVII was examined when the cells were cultured on mass scale. For this, first, the recombinant CHO cell line which was being cultured was inoculated at a density of 1.2×10⁷ cells/mL into 4 L of a production medium in each of incubation tanks which contained sodium butyrate (Cat. no. B5887, SIGMA, USA) at concentrations of 0.3, 1.0, 1.5 and 2.0 mM, respectively. The cells grown in the presence of 0.3 mM sodium butyrate were used as a control for comparison. To produce hVII, the cells were cultured at 30.0° C. for 11-18 days with the medium continuously fed at 0.5-1.0 VVD. The culturing was stopped when cellular activity was reduced to less than 80%. During the cultivation, a predetermined volume of the cell culture was taken at regular intervals of time and examined for cell density and cellular activity.

In addition, after the cell cultures taken during the cultivation was centrifuged, the levels of hFVII in the supernatants were measured using an enzyme immunoassay method as in Example <2-2>. Measurements are expressed as % of production compared to the control and summarized in Table 3, below.

TABLE 3

Production Level of hFVII according to
Concentration of Sodium Butyrate (%)

| Conc. of Na Butyrate (mM) | FVII Level (% compared to control %) | Period of Time of Production (% compared to control) |
|---|---|---|
| 0.3 | 100.0 | 100.0 |
| 1 | 154.5 | 83.3 |
| 1.5 | 157.7 | 72.2 |
| 2.0 | 127.6 | 61.1 |

When higher concentrations of sodium butyrate were added, as can be seen in Table 3, higher amounts of FVII were produced in spite of the reduced periods of time of FVII production, indicating that sodium butyrate contributes to an improvement in FVII productivity.

Example 5

Purification of Factor VII from Culture Medium

An ultrafiltration membrane (SARTOCON Slice Cassette, PESU, Sartorius, MWCO 30 K) was washed for one hour with 1 L of 1 N NaOH, washed with 5 L of sterilized water. Then, after the ultrafiltration membrane was equilibrated with a primary purification column equilibration buffer, the factor VII-expressing cell culture was loaded to the membrane and 10-fold concentrated. The concentrate was two-fold diluted with the same volume of the primary purification column equilibration buffer and then concentrated to its original volume. This dilution-concentration procedure was repeated seven times with the primary purification column equilibration buffer for the diafiltration of the cell culture. There was no loss of the factor VII during the diafiltration. The factor VII was measured to have a final concentration of 0.3 mg/mL. The ultrafiltration and diafiltration was carried out under a 4° C. condition. The diafilterd factor VII solution was finally filtered through a 0.22 μm filter (NALGENE, PES) and loaded to a column for anion exchange chromatography. In the present invention, a column filled with Q Sepharose resin (Fast Flow, GE Healthcare) was used for anion exchange chromatography. After the samples were loaded to the column, elution was performed with equilibration buffer A (20 mM Tris pH8.0+2 mM Benzamidine), wash buffer B (20 mM Tris pH8.0+2 mM Benzamidine+0.2 M NaCl), wash buffer C (20 mM Tris pH8.0+2 mM Benzamidine+0.1 M NaCl) and elution buffer D (20 mM Tris pH8.0+2 mM Benzamidine+25 mM NaCl+35 mM $CaCl_2$) in such a way that the purity of eluted protein was improved by using gradient elution with a linear gradient of from wash buffer C to elution buffer D over 2.5 column volumes. Immediately after the elution by anion exchange chromatography, the fraction containing factor VII was subjected to size exclusion chromatography to perform a buffer exchange with 20 mM Tris pH8.0+2 mM Benzamidine. The filtration, the anion exchange chromatography and the size exclusion chromatography were carried out at 4° C. The sample which was buffer exchanged by size exclusion chromatography was loaded to a column for anion exchange chromatography. The column was filled with Q Sepharose resin (High Performance, GE Healthcare). After the column was equilibrated with equilibration buffer A (20 mM Tris pH 8.0+2 mM Benzamidine), the loaded sample was eluted by using gradient elution with a linear gradient 20%-35% elution buffer B (20 mM Tris pH 8.0+2 mM Benzamidine+1 M NaCl) over 15 column volumes. The factor VII eluate was formulated with 20 mM potassium phosphate, pH 5.5, through size exclusion chromatography. All procedures were carried out at 4° C. As explained above, factor VII can be stored after being purified as an inactive form. If necessary, factor VII may be converted into the active form factor VIIa as illustrated in Example 6, below.

Example 6

Activation of Purified Factor VII

To activate factor VII, the purified factor VII sample was loaded onto an anion exchange chromatography column previously equilibrated with equilibration buffer A (20 mM Tris pH 8.0+2 mM Benzamidine). The column was filled with Source 15Q resin (GE Healthcare). After equilibration with buffer A, the sample was subjected to on-column activation for 40 min using elution buffer B (20 mM Tris pH8.0+2 mM Benzamidine+25 mM NaCl+35 mM $CaCl_2$) at a concentration of 5%, followed by isocratic elution using elution buffer B to elute the protein. The activation of factor VII was carried out at room temperature.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A method for mass production of human coagulation Factor VII, comprising:
   a) providing a Chinese hamster ovarian carcinoma cell line transfected with an expression vector, said expression vector carrying i) a dihydrofolate reductase promoter devoid of one or more CCGCCC repeat sequences from the GC-rich region and a dihydrofolate reductase gene operably linked thereto and ii) a cytomegalovirus promoter and a human coagulation Factor VII gene operably linked thereto;
   b) culturing the transfected cell line of step a) in the presence of a dihydrofolate reductase inhibitor to select cells which express human coagulation Factor VII;
   c) culturing the selected cells in a medium containing sodium butyrate in concentration from 1 mM to 1.5 mM to produce human coagulation Factor VII; and
   d) harvesting the produced human coagulation Factor VII, wherein the human coagulation Factor VII gene has the nucleotide sequence of SEQ ID NO: 3.

2. The method of claim 1, wherein the GC-rich region contains as many as or less than one CCGCCC repeating sequence.

3. The method of claim 1, wherein the expression vector is pXOGC-FVII.

4. The method of claim 1, wherein the Chinese hamster ovarian carcinoma cell line before transfection in step a), is devoid of dihydrofolate reductase gene.

5. The method of claim 1, wherein the selected cells of step c) is HMF708, which has Accession Number KCTC 11779BP.

6. The method of claim 1, further comprising purifying the human coagulation Factor VII.

7. The method of claim 1, further comprising activating the human coagulation Factor VII.

8. A cell line for producing human coagulation Factor VII, wherein said cell line is HMF708 having Accession Number KCTC 11779BP.

* * * * *